United States Patent [19]

Kotani et al.

[11] 4,403,186

[45] Sep. 6, 1983

[54] SURFACE PRESSURE MEASUREMENT TYPE MAGNETIC ANALYZER FOR PARAMAGNETIC GASES UTILIZING A MAGNETIC FIELD GENERATED ALTERNATIVELY BETWEEN PLURAL PAIRS OF MAGNETIC POLE PIECES

[75] Inventors: Haruo Kotani, Takatsuki; Tomoyuki Haga, Kyoto, both of Japan

[73] Assignee: Horiba, Ltd., Kyoto, Japan

[21] Appl. No.: 119,651

[22] Filed: Feb. 8, 1980

[30] Foreign Application Priority Data

Feb. 10, 1979 [JP] Japan .................................. 54-15576

[51] Int. Cl.³ ...................... G01N 27/74; G01R 33/12
[52] U.S. Cl. .................................... 324/204; 73/27 A
[58] Field of Search ............... 324/204, 234, 236, 262; 73/27 A

[56] References Cited

FOREIGN PATENT DOCUMENTS 2701084 7/1978 Fed. Rep. of Germany ..... 73/27 A
1415888 12/1975 United Kingdom ............... 73/27 A

*Primary Examiner*—Gerard R. Strecker
*Assistant Examiner*—Walter E. Snow
*Attorney, Agent, or Firm*—Antonelli, Terry & Wands

[57] ABSTRACT

A magnetic analyzer is provided for detecting the concentration of a paramagnetic gas, such as oxygen, in a gas being tested. This detection is based on detecting the surface-pressure generated between a gas being tested and a comparison gas. The surface-pressure is sensed by a condenser-microphone which is coupled to comparison gas passageways in two pairs of magnetic pole pieces which are inserted in a measuring chamber filled with the gas being tested and which alternately generate a magnetic field.

12 Claims, 2 Drawing Figures

SURFACE PRESSURE MEASUREMENT TYPE MAGNETIC ANALYZER FOR PARAMAGNETIC GASES UTILIZING A MAGNETIC FIELD GENERATED ALTERNATIVELY BETWEEN PLURAL PAIRS OF MAGNETIC POLE PIECES

BACKGROUND OF THE INVENTION

1. Field of the Invention

The present invention relates generally to an improvement on a magnetic analyzer of oxygen, and, in particular, to a magnetic analyzer which can determine the concentration of oxygen in a gaseous sample from the variation of surface-pressure owing to the difference in magnetizing coefficients.

2. Description of the Prior Art

Magnetic analyzers of oxygen are classified roughly into those of the heat ray type and those which make use of variations in surface-pressure.

The former type is an analyzer which makes use of the cooling of heated rays and applies the principle that a magnetizing coefficient of oxygen, which is a paramagnetic gas, is reduced with a rise of temperature in accordance with Curie's law. That is to say, if heat rays arising from Joule heat or the like are located in an unequal magnetic field formed by a strong magnet in a measuring chamber made of non-magnetic materials, magnetic force is generated with a strength that is in proportion to the content of oxygen. Consequently, heat rays located in a magnetic field are cooled excessively compared with those not located in the magnetic field by virtue of such magnetic forces. On the basis of the above-mentioned principle, the concentration of oxygen in a gaseous sample can be determined by detecting the difference of temperature between these heat rays.

Accordingly, in the analyzers of this heat ray type, the measurement is remarkably influenced by the variation of thermal properties of coexistent gases. For example, the thermal conductivity and specific heat when hydrogen and carbon dioxide are present are remarkably different from oxygen alone. Such coexistent gases can be present in great quantities, and their contents are varied at times. Moreover, the analyzers of this type have a defect in that some special safety countermeasures are required against explosion in a case where the concentration of oxygen in explosive gases is measured because the temperature of heat rays is comparatively high.

The latter type of analyzer (i.e. the type which makes use of the variation in surface-pressure) is superior to the heat ray type in the above-mentioned points, and a high practical value can be expected for it.

The analyzers of the surface-pressure type apply the following principle. As shown in FIG. 1, a minute quantity of non-magnetic gas (for example, pure nitrogen), or a mixture of paramagnetic gases and non-magnetic gases (for example, air), is introduced into a passageway "a" of gases to be measured as a suitable comparison gas through a minute hole 6. This hole 6 is provided on one magnetic pole N in the portion where the magnetic poles N and S are arranged in said passageway "a" of gases to come closest each other so that the strongest magnetic field is formed.

In such a case, it has been known that kinetic pressure P, expressed by the following Quinke's equation, is generated in a vertical direction relative to boundary surfaces "b" and "c" between the comparison gas and the gas to be measured if the gases at said boundary surfaces "b" and "c" have magnetizing coefficients of $x_1$ and $x_2$, which respectively exist in said magnetic field having the strength of H:

$$P = K(x_1 - x_2)H^2 \qquad (1)$$

where K is a constant including elements such as temperature; $x_2$ is the magnetizing coefficient of the comparison gas; and $x_1$ is the magnetizing coefficient of the gas to be measured. In a case when the condition of $x_1 > x_2$ is satisfied, the surface-pressure is generated on the boundary surface between $x_1$ and $x_2$ in the direction from $x_1$ to $x_2$.

Accordingly, if the strength of said magnetic field H and any one of said magnetizing coefficients $x_1$ and $x_2$ are held constant, the magnetizing coefficient of another gas can be determined from the variation of said surface-pressure P. Then the content of a paramagnetic gas, such as oxygen, in the gas to be measured can be determined from the magnetizing coefficient.

However, all of the conventional analyzers of the surface-pressure type consist of one pair of magnetic pole pieces which face each other in the measuring chamber at a minute distance and one pair of false pole pieces made of non-magnetic materials having the same shape and size as said magnetic pole pieces. In such analyzers the variation of surface-pressure owing to the difference in magnetizing coefficients has been detected from the pressure inside a passageway of the comparison gas provided on one side of said magnetic pole pieces and the pressure inside a passageway of the comparison gas provided on one side of said false pole pieces which corresponds to said magnetic pole piece mentioned above. Consequently, the variation of surface-pressure owing to the difference in magnetizing coefficients is remarkably small, for example only 2 to $3 \times 10^{-1}$ microbar per 1% $O_2$. As a result, the measurement by means of the conventional techniques is quite difficult, and often led to error.

This is particularly the case in an analyzer in which the variation of surface-pressure is detected by a condenser-microphone. In such a case, the S/N ratio of the signal introduced in the oxygen content indicating portion is large because the variation of surface-pressure is minute. Also, although the voltage to be loaded on said condenser-microphone should be high in order to transform this minute variation of surface-pressure directly into an electrical output with high accuracy and high speed, it is known that the maximum possible voltage which can be loaded on said condenser-microphone is dependent upon the distance between a fixed pole and a condenser-film which serves as a movable pole, and upon the tension of said condenser-film. If a voltage higher than said maximum allowable voltage is loaded, the condenser-film is bent. Consequently, the distance between poles is shortened to start an electric discharge. In other words, Coulomb force hinders the possibility of increasing the voltage which can be loaded.

SUMMARY OF THE INVENTION

It is, therefore, the object of the present invention to eliminate the above-mentioned defects of conventional magnetic analyzers of oxygen of the surface-pressure measurement type.

DETAILED DESCRIPTION OF THE PREFERRED EMBODIMENTS

Figure 1:
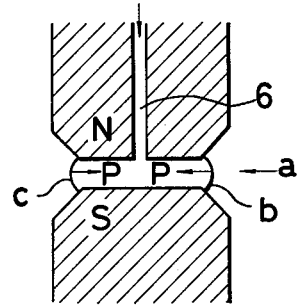
FIG. 1 shows the principle of measurement by a magnetic analyzer of oxygen of the surface-pressure measurement type.
Figure 2:
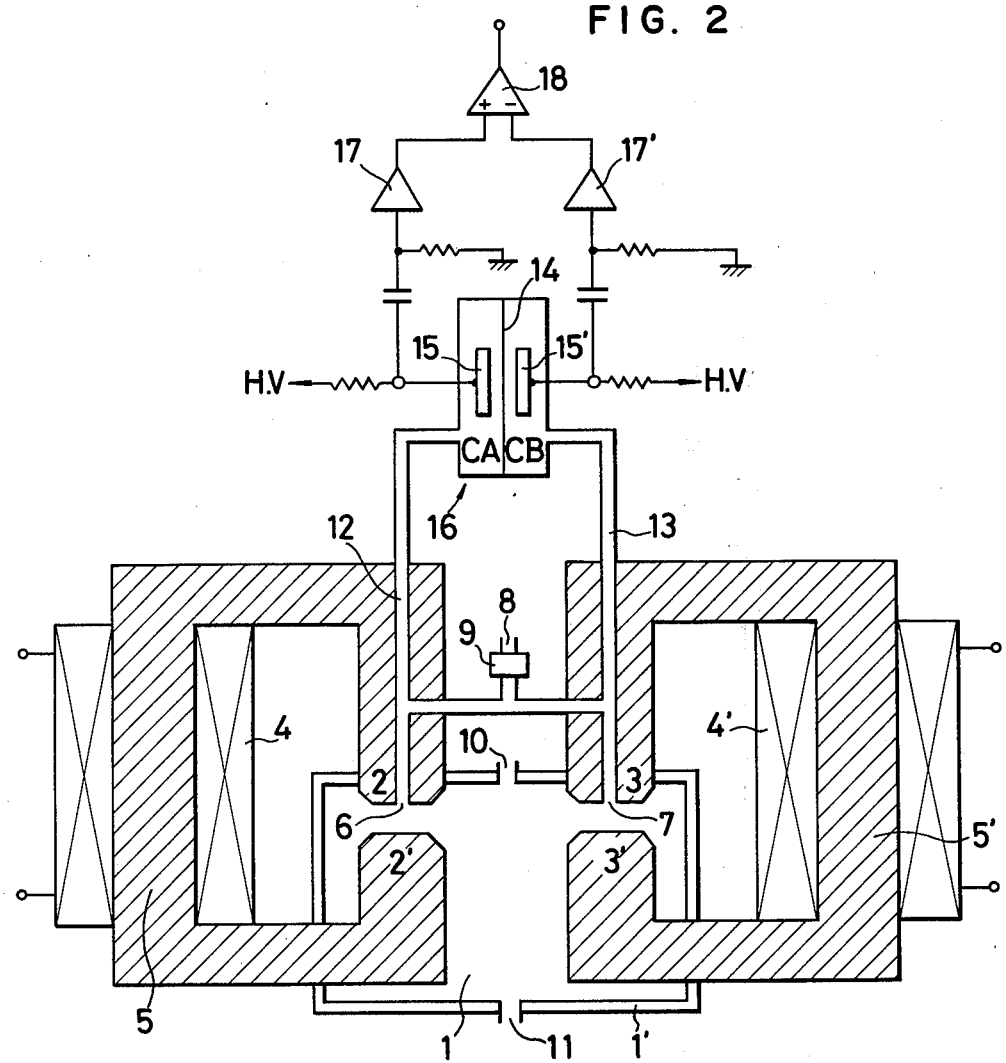
FIG. 2 shows the construction of one of the preferred embodiments of the present invention.

Referring now to FIG. 2, one of the preferred embodiments of the present invention will be described below.

In FIG. 2, two pairs of magnetic pole pieces 2-2', 3-3' face each other at a distance of a minute gap in a measuring chamber 1 surrounded by the wall 1' made of non-magnetic materials. A strong magnetic field is generated between said magnetic pole pieces 2 and 2' as well as between said magnetic pole pieces 3 and 3' through a connective iron 5, 5' by alternatively passing an electric current through electromagnetic coils 4, 4'. Holes 6, 7 for discharging a comparison gas are provided on the same side magnetic pole pieces 2, 3.

A comparison gas introduced from an inlet 8 through a flow-rate adjusting device 9 is divided into said magnetic pole pieces 2, 3 and then introduced into said measuring chamber 1 through said minute gap provided between said magnetic pole pieces 2 and 2' as well as between said magnetic pole pieces 3 and 3'.

The gas to be measured is introduced into said measuring chamber 1 through an inlet 10. An outlet is shown by 11.

The magnetic pole pieces 2, 3 are provided with pressure introducing passageways 12, 13 opening into said holes 6, 7 for discharging a comparison gas. These pressure introducing passageways 12, 13 open into chambers $C_a$ and $C_b$ which are provided on both sides of a condenser-film 14 in a condenser-microphone 16 consisting of said condenser-film 14 and two fixed poles 15, 15' which face each other on both sides of said condenser-film 14. Said condenser-microphone 16 should have an electrostatic capacity of about 50 PF and the sensibility expressed by the variation of electrostatic capacity for a minute difference in pressures inside of both sides of said condenser-film 14 of $\Delta C = 0.0001.PF$. Besides, the fixed poles 15, 15' face each other on both sides of said condenser-film 14, and, consequently, Coulomb forces act in reverse directions to each other between said pole 15 and said condenser-film 14 as well as between said pole 15' and said condenser-film 14. As a result, contrary to the conventional condenser-microphone with a single fixed pole, Coulomb force which hinders the possibility that the voltage to be loaded on said condenser-microphone is heightened can be eliminated. Therefore, a high voltage can be loaded.

After the signals taken out from said fixed poles 15, 15' of said condenser-microphone 16 are amplified by the amplifier 17 and 17', respectively, they are added by a differential amplifier 18 and then are introduced into an oxygen content indicating portion not shown in the figure.

The case where pure nitrogen is used as the comparison gas will now be explained as an example. If the gas to be measured is pure nitrogen, the magnetic surface-pressure is not generated. Instead, only the back pressure acts, and the difference between the surface-pressure in the space of said magnetic pole pieces 2-2' and that in the space of said magnetic pole pieces 3-3' is zero because both the comparison gas and the gas to be measured have the same magnetizing coefficient. The minute gaps between said magnetic pole pieces 2 and 2' as well as between said magnetic pole pieces 3 and 3' are adjusted so that the variation of an electrostatic capacity of said condenser-microphone 16 may be zero under the state that said difference of surface-pressures is zero.

Then, if the gaseous mixture containing oxygen is introduced into said measuring chamber 1 as the gas to be measured, an electric current is passed through said electromagnetic coil 4 and 4' alternatively. Consequently, strong magnetic fields are alternatively generated in the space between said magnetic pole pieces 2 and 2' and between said magnetic pole pieces 3 and 3'. As a result, surface-pressure is generated in proportion to the difference between the magnetizing coefficient of the gas to be measured and that of the comparison gas alternatively in a minute gap between said magnetic pole pieces 2 and 2' and a minute gap between said magnetic pole pieces 3 and 3'. Accordingly, such alternatively generated surface pressures are transmitted to said condenser-microphone 16 through said pressure introducing passageways 12, 13 to push said condenser-film 14 in the form of a differential pressure between the space between said magnetic pole pieces 2 and 2' and that between said magnetic pole pieces 3 and 3'.

Such a surface-pressure is expressed as follows on the basis of the above-mentioned equation (1):

$$P_{2\text{-}2'} = K_1(x_1 - x_2)H_1^2 \qquad (2)$$

$$P_{3\text{-}3'} = K_2(x_1 - x_2)H_2^2 \qquad (3)$$

where
$P_{2\text{-}2'}$ and $P_{3\text{-}3'}$ are surface-pressures generated between said magnetic pole pieces 2 and 2' and between said magnetic pole pieces 3 and 3', respectively;
$K_1$ and $K_2$ are constants including elements such as temperature;
$x_1$ and $x_2$ are magnetizing coefficients of the gas to be measured and the comparison gas, respectively; and
$H_1$ and $H_2$ are the strengths of the magnetic fields generated between said magnetic pole pieces 2 and 2' and between said magnetic pole pieces 3 and 3', respectively.

The dislocation of said condenser-film 14 in said condenser-microphone 16 is put out from each fixed pole 15, 15' in the form of the variation of electrostatic capacity between said condenser-film 14 and said fixed poles 15, 15', respectively. Therefore, if the output signals on the basis of $P_{2\text{-}2'}$ and $P_{3\text{-}3'}$ are added by said differential amplifier 18, in a case when $K_1 = K_2 = K$, $H_1 = H_2 = H$, $x_2$ (pure nitrogen) $= 0$ the pressure P can be expressed as follows:

$$P \simeq P_{2-2'} + P_{3-3'} = 2K \cdot x_1 \cdot H^2 \qquad (4)$$

$$= 2K \cdot K' \cdot C \cdot H^2 = \mathbb{K} \cdot C \cdot H^2 \qquad (5)$$

where C is the concentration of oxygen in the gas to be measured and $X_1$ is in proportion to C. K' and $\mathbb{K}$ are constants.

As understood from the equations (4) and (5), the quantity of the output signal can be doubled by adding by means of said differential amplifier and the concentration of oxygen is indicated on the basis of this doubled signal.

Namely, in the present invention, not only a high voltage can be loaded on said condenser-microphone 16, but also the quantity of the output signal can be doubled by adding by means of said differential amplifier. As a result, the noise introduced from the outside as well as the noise due to an alternative current included in the power source can be lowered. Also, the S/N ratio can be remarkably improved. Thus, the concentration of oxygen can be determined with high accuracy on the basis of a minute variation of surface-pressure.

As shown above, according to the present invention, the measurement is not affected by the variation of thermal properties of coexistent gases and its stability is high. Besides the abovementioned effects, the following effects are produced: the quantity of the signal accompanied with a minute variation of surface-pressure can be doubled; the noise can be reduced; and the S/N ratio can be remarkably improved. Therefore, the concentration of oxygen can be detected with a high sensibility and with high speed.

All of the above-mentioned effects arise from the fact that said surface-pressure as determined on the basis of the difference of magnetizing coefficients is detected by a condenser-microphone consisting of one condenser-film and two fixed poles which are located on both sides of said condenser-film. This determination is of the differential pressure between two pairs of magnetic pole pieces. The thus detected output signals are added by the differential amplifier and then the concentration of oxygen is determined by measuring the quantity of said output signal.

It is to be understood that the above-described arrangements are simply illustrative of the application of the principles of this invention. Numerous other arrangements may be readily devised by those skilled in the art which embody the principles of the invention and fall within its spirit and scope.

We claim:

1. A magnetic paramagnetic gas analyzer including a measuring chamber for containing a gas to be measured and a comparison gas, wherein the concentration of paramagnetic gas in the gas to be measured is detected from a surface-pressure generated within the measuring chamber between the gas to be measured and the comparison gas, said surface-pressure being due to a difference of magnetizing coefficients of the gas to be measured and the comparison gas passing through magnetic fields generated alternatively between first and second pairs of magnetic pole pieces located within said measuring chamber, and wherein said surface-pressure is detected by a condenser-microphone coupled by first and second pressure introducing passageways to the measuring chamber, said condenser-microphone comprising a condenser-film and a pair of fixed poles located such that one of said pair of fixed poles is coupled to said measuring chamber by the first pressure introducing passageway and is on one side of said condenser-film, and the other of said pair of fixed poles is coupled to said measuring chamber by the second pressure introducing passageway and is on the other side of said condenser-film, so that said surface-pressure is detected using said pair of fixed poles, said detection being performed on the basis of a differential pressure between the two pairs of magnetic pole pieces when a magnetic field is generated alternatively between the two pairs of magnetic pole pieces.

2. The magnetic paramagnetic gas analyzer according to claim 1 wherein said measuring chamber is surrounded by a wall of nonmagnetic materials.

3. The magnetic paramagnetic gas analyzer of claim 1, wherein one magnetic pole piece of said first pair of magnetic pole pieces is provided with a first hole for discharging the comparison gas and is also provided with said first pressure introducing passageway having one end which opens into said first hole for discharging the comparison gas and another end which opens into a chamber containing said one fixed pole located on one side of said condenser-film, and wherein one magnetic pole piece of said second pair of magnetic pole pieces is provided with a second hole for discharging the comparison gas and is also provided with said second pressure introducing passageway having one end which opens into said second hole for discharging the comparison gas and another end which opens into a chamber containing said other fixed pole located on said other side of said condenser-film.

4. The magnetic paramagnetic gas analyzer according to claim 1, wherein the pairs of magnetic pole pieces are part of a pair of electromagnets, and further wherein the alternately generated magnetic field is generated by alternately passing electric current through electromagnetic coils wound on said electromagnets.

5. The magnetic paramagnetic gas analyzer according to claim 1, wherein the paramagnetic gas is oxygen.

6. A magnetic paramagnetic gas analyzer according to claim 1, wherein said one fixed pole is located in a first chamber which is coupled to said first gas pressure introducing passageway, said first gas pressure introducing passageway also having an opening adjacent to said first pair of magnetic pole pieces, and wherein said other fixed pole is located in a second chamber which is coupled to said second gas pressure introducing passageway, said second gas pressure introducing passageway also having an opening adjacent to said second pair of magnetic pole pieces.

7. A magnetic paramagnetic gas analyzer according to claim 1, further comprising means for loading a voltage onto said pair of fixed poles and a differential amplifier coupled to said pair of fixed poles with a non-inverting input terminal of said differential amplifier being coupled to said one fixed pole and an inverting input terminal of said differential amplifier being coupled to said other fixed pole.

8. A magnetic paramagnetic gas analyzer for determining the paramagnetic gas concentration in a gas to be measured within a measuring chamber comprising:
    first and second pairs of magnetic pole pieces located in the measuring chamber;
    means to inject said gas to be measured into said measuring chamber;
    means to inject a comparison gas having a magnetizing coefficient which is different than a magnetizing coefficient of said gas to be measured into said measuring chamber;
    means to generate magnetic fields alternatively at said first and second pairs of magnetic pole pieces to produce a surface-pressure along a boundary surface within said measuring chamber between said gas to be measured and said comparison gas due to the difference between the magnetizing coefficients of said gas to be measured and said comparison gas; and
    means to measure the surface-pressure which develops along said boundary between the comparison gas and the gas to be measured during the alternative generation of magnetic fields at the first and second pairs of magnetic pole pieces to provide an indication of the concentration of said paramagnetic gas in said gas to be measured within said measuring chamber based on the measured strength of said surface-pressure.

9. A magnetic paramagnetic gas analyzer according to claim 8, wherein the means to inject the comparison gas comprises a first passageway located in one pole piece of the first pair of magnetic pole pieces opening into the measuring chamber and a second passageway located in one pole piece of the second pair of magnetic pole pieces opening into the measuring chamber.

10. A magnetic paramagnetic gas analyzer according to claim 9, wherein the first and second passageways open into the measuring chamber at the gaps between the respective pole pieces of the first and second pairs of magnetic pole pieces.

11. A magnetic paramagnetic gas analyzer according to claim 8, wherein the surface pressure measuring means comprises:
a condenser-film;
a first chamber on one side of the condenser-film coupled to a first passageway having an opening adjacent said first pair of magnetic pole pieces;
a second chamber on the other side of the condenser-film coupled to a second passageway having an opening adjacent said second pair of magnetic pole pieces;
a first fixed pole piece located in the first chamber;
a second fixed pole piece located in the second chamber; and
means coupled to the first and second fixed pole pieces to measure the variations in the electrostatic capacity between the condenser-film and the first and second fixed poles.

12. A magnetic paramagnetic gas analyzer according to claim 8, wherein the paramagnetic gas is oxygen.

* * * * *